United States Patent [19]

Strandberg

[11] Patent Number: 5,277,928
[45] Date of Patent: Jan. 11, 1994

[54] METHOD AND APPARATUS FOR CONTROLLING YARN COATINGS

[76] Inventor: John A. Strandberg, 1700 Independence Rd., Greensboro, N.C. 27408

[21] Appl. No.: 726,271

[22] Filed: Jul. 5, 1991

[51] Int. Cl.$^5$ .......................... B05D 3/12; B05C 11/00
[52] U.S. Cl. ........................................... 427/10; 427/8; 427/175; 427/394; 427/434.2; 427/434.4; 427/434.6; 118/665; 118/680; 118/712; 118/713; 118/420
[58] Field of Search ............... 118/665, 680, 712, 665, 118/713, 420; 427/8, 10, 434.2, 434.4, 434.6, 394, 175

[56] References Cited

U.S. PATENT DOCUMENTS

| 3,207,125 | 9/1965 | Strandberg, Jr. | 118/665 |
|---|---|---|---|
| 3,751,893 | 8/1973 | Goodhue et al. | 57/34 |
| 3,803,822 | 4/1974 | Mulligan | 57/34 |
| 3,862,553 | 1/1975 | Schwemmer et al. | 118/665 X |
| 3,902,308 | 9/1975 | Berstein et al. | 57/34 |
| 3,945,181 | 3/1976 | Yamazaki et al. | 57/34 |
| 4,541,236 | 9/1985 | Dallolio | 57/264 |
| 4,587,801 | 5/1986 | Missout et al. | 57/6 |
| 4,648,054 | 3/1987 | Farah et al. | 364/552 |
| 4,660,365 | 4/1987 | Raasch | 57/263 |
| 4,738,866 | 4/1988 | Conklin et al. | 118/712 X |
| 4,891,974 | 1/1990 | Wassenhoven | 73/160 |
| 5,043,590 | 11/1991 | Strandberg et al. | 250/571 |
| 5,072,691 | 12/1991 | Strandberg et al. | 118/679 |

OTHER PUBLICATIONS

Strandberg The Moisture Monitor brochure (undated).
Strandberg The Densitek I Fabric Density Sensor brochure (undated).
Strandberg The Stretch Monitor brochure (undated).

Primary Examiner—Janyce Bell

[57] ABSTRACT

An apparatus and method for controlling yarn coatings such as sizing are provided which includes nuclear radiation detectors which measure the attenuated radiation through processed yarn. Before and after radiation measurements are signaled to a computer which is programmed to generate a signal which controls squeeze rollers that adjust, according to specific size requirements. A second embodiment of the invention is provided for processing tire cord webs and utilizes digital line scan cameras in conjunction with the radiation detector sensors. Line scan cameras provide an opacity measure to determine yarn count and maintain an accurate density measurement even as lateral shifts in the web during processing occur.

29 Claims, 5 Drawing Sheets

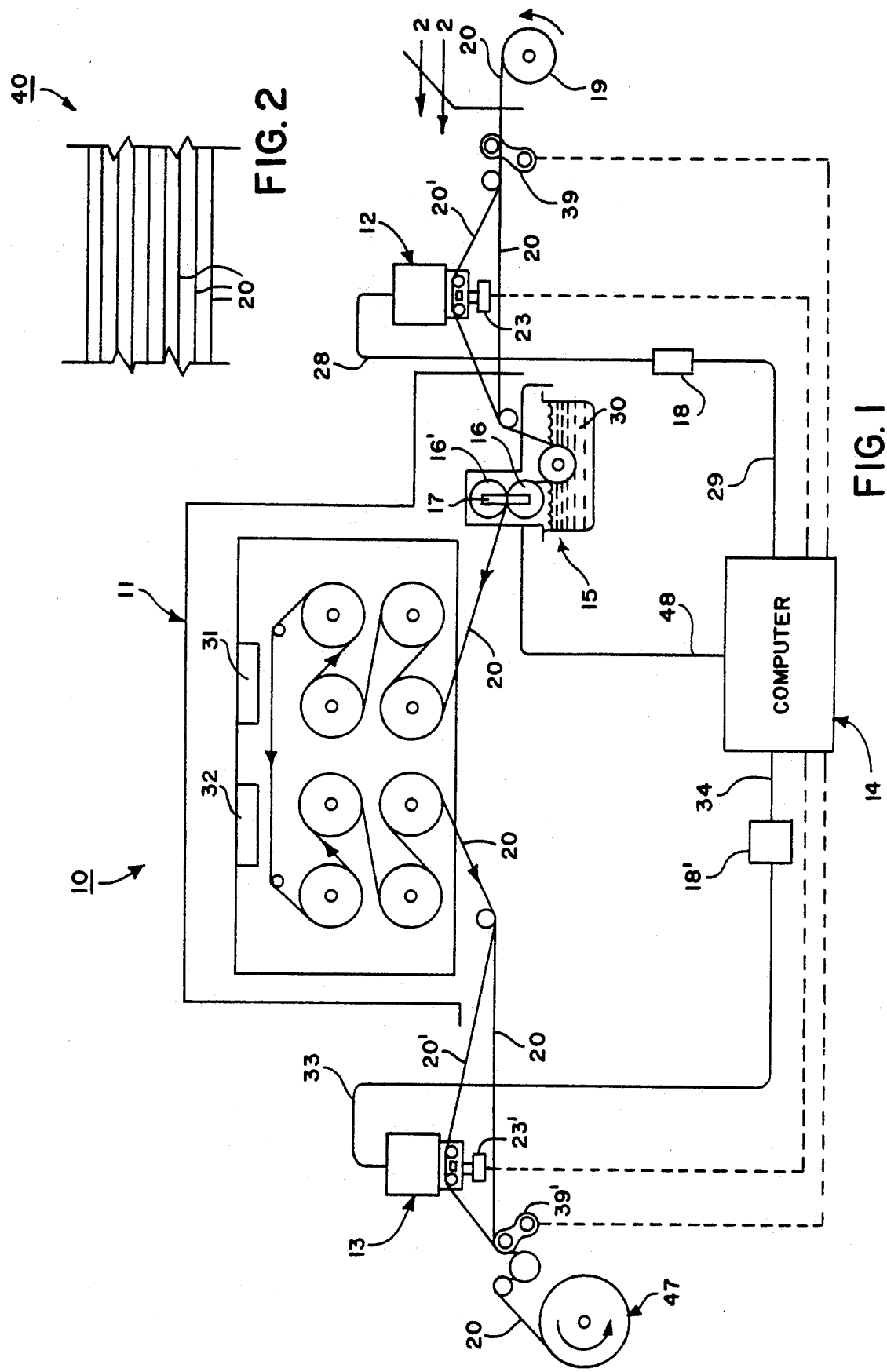

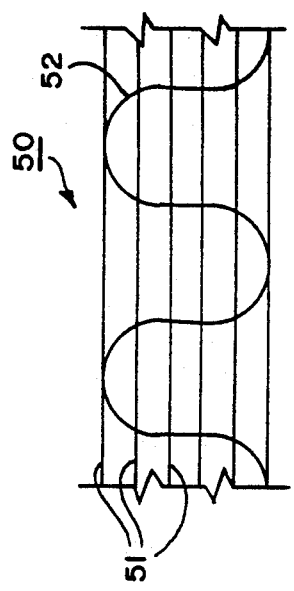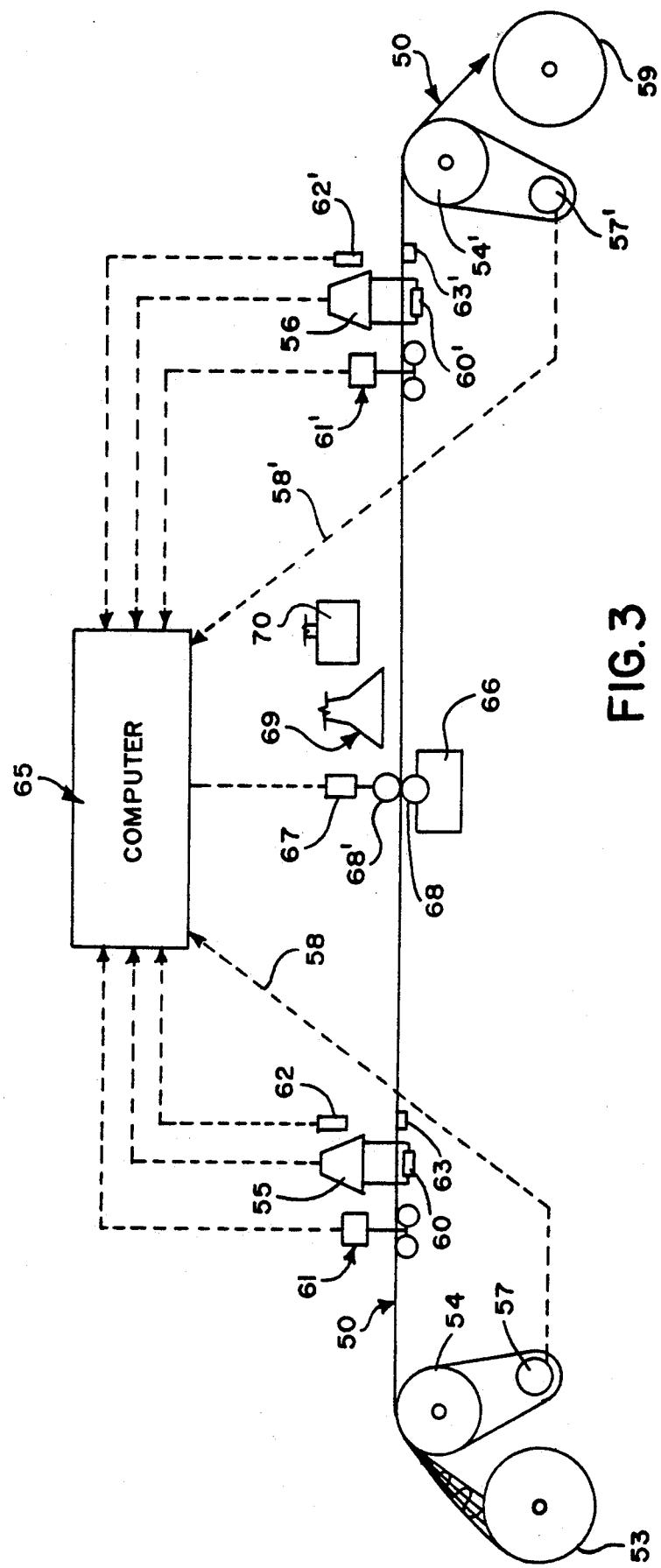

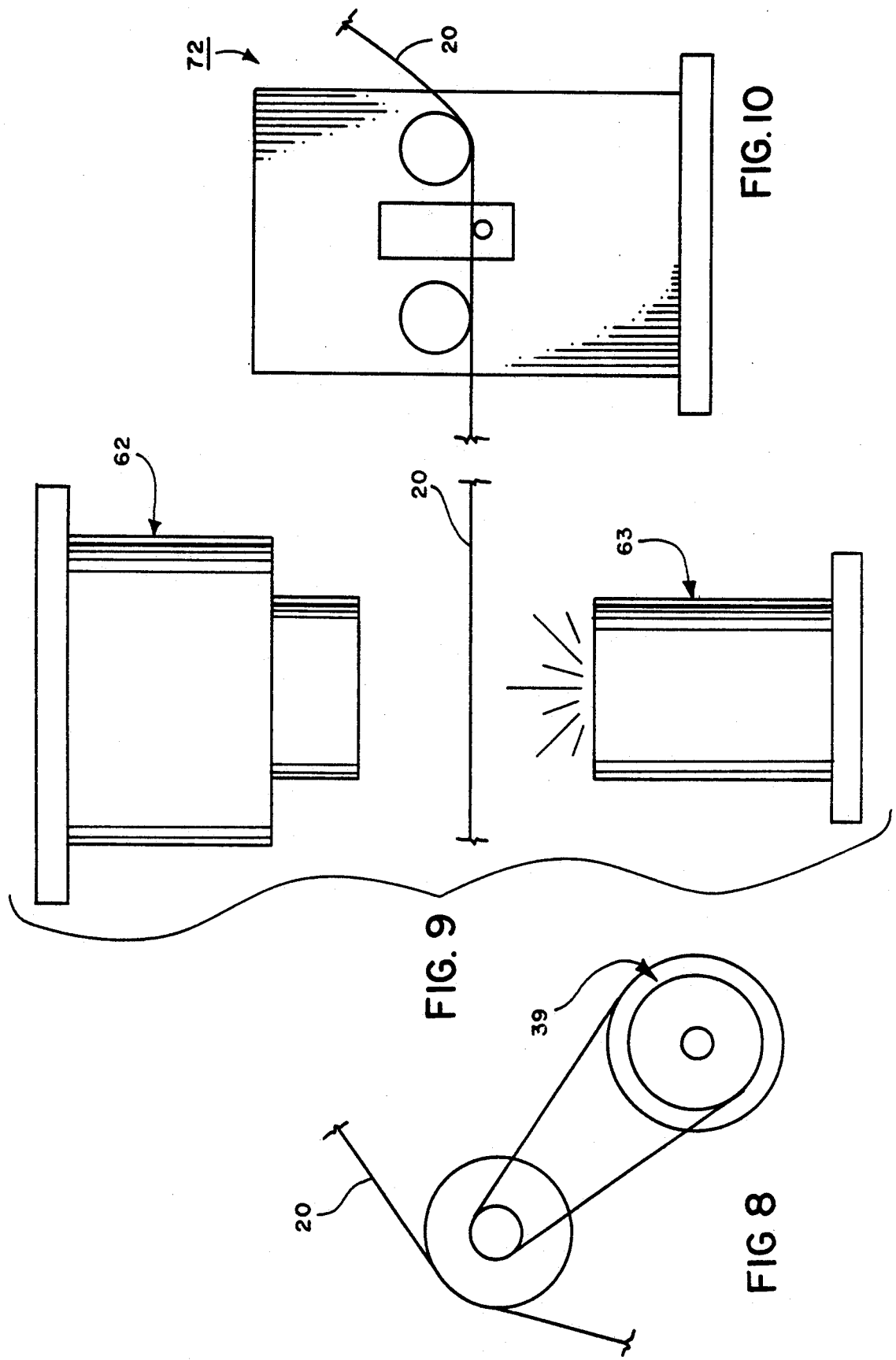

METHOD AND APPARATUS FOR CONTROLLING YARN COATINGS

BACKGROUND OF THE INVENTION

1. Field of the Invention

The invention herein pertains to application and control of coatings to yarn, yarn webs and the like in continuous processes. The method and apparatus described herein are particularly useful in the field of textile yarn coatings and in preparing cord webs for vehicle tire manufacturing.

2. Description of the Prior Art and Objectives of the Invention

Various types of coatings such as sizing are applied to textile yarns and must be carefully monitored during application. Weaving and other subsequent operations are greatly influenced by the amount of starch or other sizing components on the yarn. Also, the efficiency by which the fabric is woven severely affects the ultimate fabric cost. Thus, too little or too much sizing applied can affect both the convenience and economics of later processing operations while excess amounts of sizing result in higher chemical costs during manufacturing. As a result, various instruments have been developed in the past for controlling the sizing applied to yarn during continuous yarn processing procedures. Both off-line and on-line instruments have been used for measuring weight, elongation of yarn (stretch), and moisture (retention) in an effort to better control the coatings applied. While such prior art devices have met with limited success, they have not permitted coating applications generally to only vary in the single digit percentage range. With increased competition from foreign textile manufacturers who produce goods with relatively low labor costs, the present invention was conceived and one of its objectives is to provide a method and apparatus for controlling the coating of yarn which will insure a uniform application over an extended run and the most accurate amount of coating pick-up.

It is still another objective of the present invention to provide a method to control the coating of yarn in order to achieve a greater efficiency in weaving and subsequent yarn operations.

It is yet another objective of the present invention to provide apparatus for controlling the coating of yarn which includes a moisture monitor and elongation measure for more greater accuracy.

It is also another objective of the present invention to provide a method and apparatus for controlling the coating of tire cord webs during on-line processing without the necessity of stopping the web for measurements or for equipment adjustment purposes.

It is yet still another objective of the present invention to provide a method and apparatus for coating yarn which includes the use of nuclear density sensors, digital cameras for opacity measurements, moisture detectors, encoders for the measurement of yarn elongation and microprocessor circuitry for sizing application equipment control.

Various other advantages and benefits of the present invention will become apparent as the details of the invention are presented below.

SUMMARY OF THE INVENTION

The aforesaid and other objectives are realized by providing apparatus in one embodiment for sensing the density of yarn prior to entry of a slasher or other size applicator, and after the yarn has been coated and dried a second or exit sensor measures the density of the coated yarn. A microprocessor or computer receives electrical signals from both the entry and exit yarn sensors and thereafter forwards a signal to squeeze rollers within the slasher to adjust the size application. By microprocessor programming techniques, entry and exit yarn sensor signals which are received by the microprocessor along with signals from yarn moisture sensors and signals from an encoder for stretch measurement, calculations are performed to enable the squeeze rollers to either loosen or tighten to respectively maintain or reduce the size on the yarn as required. In a second embodiment of the invention, used in the manufacture of vehicle tires, digital line scan cameras are positioned behind the entry and exit sensors during the tire cord web processing for providing an opacity measurement which functions as an inferred end or yarn count to accommodate lateral web shifts which cause the number of ends under each sensor to change during processing. Thus, the line scan cameras increase the accuracy of the calculation performed by the microprocessor and insure proper adjusting vacuum pressures for control of the size extraction rate from the processed web.

BRIEF DESCRIPTION OF THE DRAWINGS

FIG. 1 demonstrates in schematic fashion the apparatus of the invention for controlling the coating on a typical conventional textile yarn;

FIG. 2 demonstrates a schematic top plan view of the yarn web as shown in FIG. 1;

FIG. 3 illustrates apparatus as used in coating tire cord webs;

FIG. 4 demonstrates a schematic top plan view of the web as processed by the equipment shown in FIG. 3;

FIG. 8 shows an encoder for measuring elongation or stretch of yarn;

FIG. 9 demonstrates a digital camera for opacity measurements;

FIG. 10 demonstrates a yarn evenness sensor for yarn diameter measurements;

DESCRIPTION OF THE PREFERRED EMBODIMENTS

The preferred apparatus and method of the invention is best illustrated in FIG. 1. As shown therein, continuous unsized yarn from a creel moves past a nuclear radiation detection sensor having a pair of v-pulleys for guiding yarn therethrough. One or more ends of yarn are fed through the pulley and by the use of a radioactive isotope such as Technetium 99 which is contained within the sensor, yarn radiation occurs and attenuated radiation is measured and a proportional electric signal is generated. The entry radiation detection sensor is connected to a circuit board which amplifies and linearizes the generated signal from the sensor prior to receipt by a microprocessor or computer. As the yarn continues to pass the entry yarn sensor it enters a slasher where the yarn is sized, moisture extracted and is then dried prior to slasher exit. As the yarn leaves the slasher it encounters a second or exit nuclear radiation detection yarn sensor where the yarn is again radiated by Technetium 99. An electric signal from the ion chamber of the sensor is transmitted to an exit sensor board which amplifies and linearizes the signal before directing it to the computer. The computer is programmed to compare the entry yarn sensor signal with the exit yarn sensor signal to thereby regulate the squeeze roller pressure in the slasher size box to either maintain or reduce the amount of size on the yarn. The computer, by determining the difference between the yarn densities before and after sizing adjusts the coating application accordingly to provide the most efficient size pick-up. Signals are simultaneously fed from conventional moisture meters and encoders which determine stretch or elongation of the yarn and a yarn evenness sensor which are taken into account by the microprocessor program in adjusting the squeeze roll pressure for proper size control.

DETAILED DESCRIPTION OF THE DRAWINGS AND OPERATION OF THE INVENTION

Figure 7:
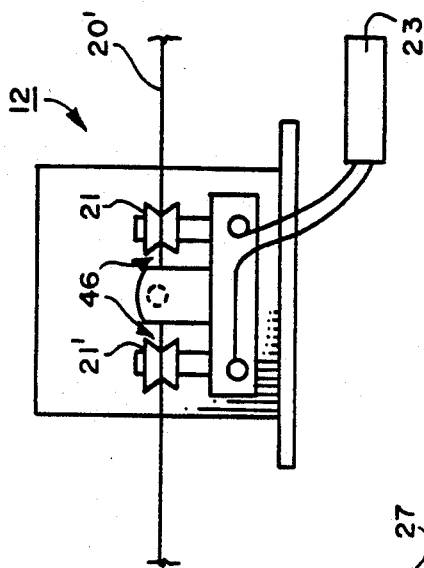
FIG. 7 shows a bottom plan view of the nuclear detector as shown in FIG. 5.
Figure 6:
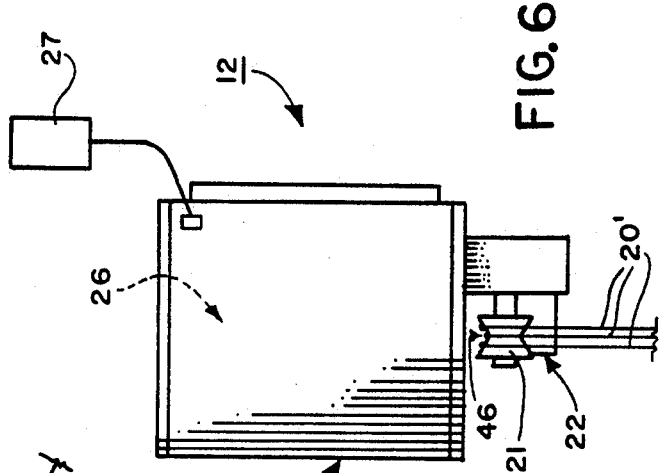
FIG. 6 shows a end view of the detector sensor as shown in FIG. 5.
Figure 12:
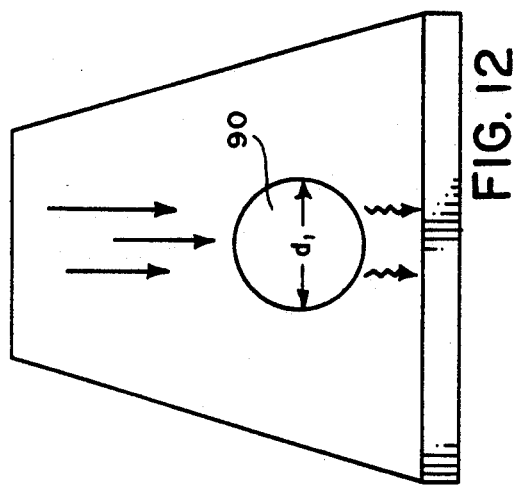
FIG. 12 pictures a cross-sectional view of a yarn strand before size encapsulation.
Figure 13:
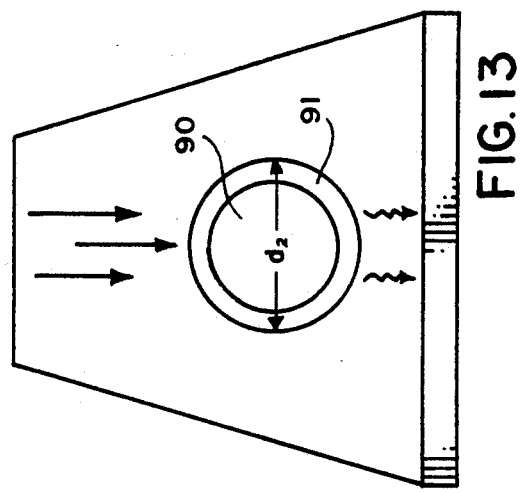
FIG. 13 shows the yarn strand in FIG. 12 after size encapsulation and penetration into the strand.
Figure 11:
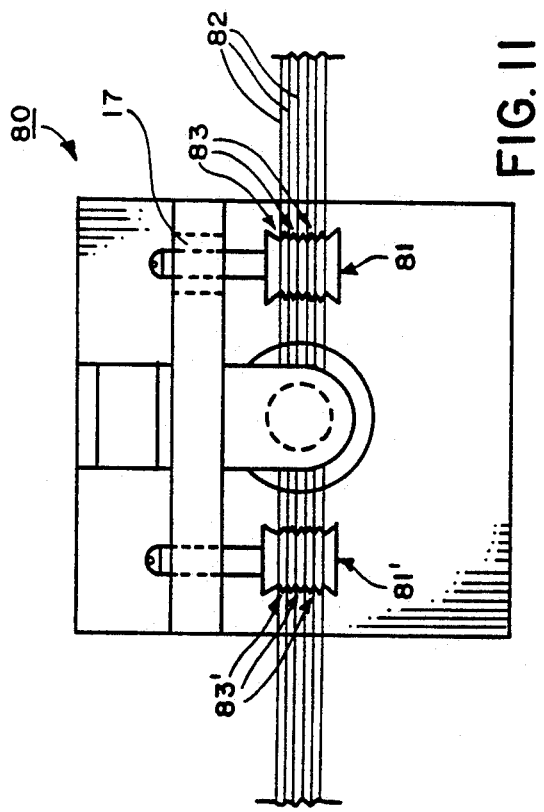
FIG. 11 depicts another embodiment of a yarn sensor.

For a more complete understanding of the invention and its method of operation, turning now to the drawings, coating apparatus 10 is shown in FIG. 1 which includes slasher 11, entry nuclear detection sensor 12 and exit nuclear detection sensor 13. Computer 14 which includes conventional microprocessor circuits provides a means for processing data from nuclear sensors 12 and 13, and is in communication therewith. Computer 14 is also in communication with size box 15 and controls the same. The pressure between squeeze rollers 16, 16' is regulated by conventional size box controls 17 connected to computer 14. Circuit boards 18, 18' as shown in FIG. 1 amplify and linearize signals from nuclear entry sensor 12 and nuclear exit sensor 13 respectively. Thus, in a typical textile yarn sizing operation, creel 19 which may contain several hundred "ends" or yarn strands 20 is rotatably mounted to allow strands 20 to move from right to left as shown in FIG. 1 whereby one or more ends 20' are separated froms ends 20 and are directed into nuclear entry sensor 12. As seen in FIGS. 6 and 7, sensor 12 includes a pair of pulleys 21, 21' each having a v-shaped pulley groove 46 for receiving and containing one or more yarn strands 20'. Pulleys 21, 21' serve a dual purpose in that they provide a positive means to guide yarn strands 20' therethrough over radioactive source 22, and are also in electrical communication with moisture meter 23. Thus, strands 20' passing through nuclear detection sensor 12 are both radiated and checked for moisture simultaneously. In FIG. 11 nuclear detector sensor 80 is illustrated having pulley 81, 81' thereon. Sensor 80 is identical to sensors 12 and 13 with the exception of sensor pulleys 81, 81' which comprise a plurality of relatively shallow grooves 83, 83' for guiding or supporting yarn strands 82. As seen in FIG. 11, five (5) grooves are provided although more or less may be desired, depending on the particulars of sensor 80. Conventional yarn evenness sensors 43 as seen in FIG. 10 may also be utilized when substantially rough or uneven yarns are processed and to measure yarn diameter change due to the size material encapsulating the yarn. As shown in FIGS. 12 and 13 a cross section of yarn strand 90 is radiated before (FIG. 12) and after (FIG. 13) sizing add-on. As seen, size 91 encapsulates yarn strand 90 and penetrates therein, for example during processing a braided or natural yarn such as cotton. Thus, density calculation must take into account the increased density of the yarn due to size penetration, and the added diameter of the yarn as compared to an entry yarn.

As would be understood, exit nuclear detection sensor 13 is substantially the same as entry nuclear detection sensor 12 with the exception of its location on coating apparatus 10. One or more yarn strands 20' can be directed onto pulleys 21, 21'. Both exit yarn sensor 13 and entry yarn sensor 12 utilize the same number of strands 20' during processing to provide accurate comparison results and signal transmissions to computer 14.

Figure 5:
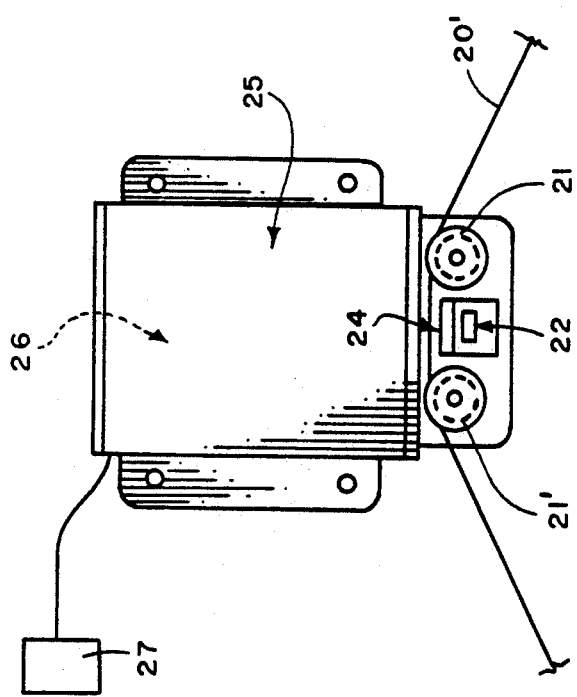
FIG. 5 illustrates a nuclear detection sensor.
Figure 14:
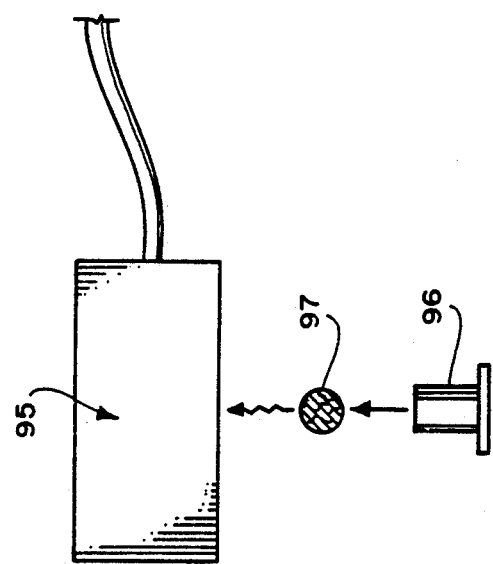
FIG. 14 illustrates in schematic fashion a conventional solid state scintillation radiation detector as used herein in yarn processing.

As seen in FIGS. 5, 6 and 7, yarn passing across pulleys 21, 21' passes over radioactive source 22 which comprises a radioactive isotope such as Technetium 99 or Promethium 147. These two isotopes have been selected because of their energy distribution which is not greater than 0.3 MeV in penetration power (beta particles). In other applications, various radioactive isotopes may be employed such as Krypton 85 having a penetration power or energy distribution of approximately 0.67 MeV., depending on the particular penetration power necessary. In FIG. 6, three strands 20' are passed across v-shaped pulley 21 although one or more strands may be used depending on the particular size strands, isotopes and pulley dimensions utilized. A conventional open-closed adjustable radiation shutter 24 is shown in FIG. 5 which permits safety closure to limit the radiation from source 22 when not in operation. Sensor housing 25 as shown in FIGS. 5 and 6 enclose conventional ionization chamber 26 therein. Other types of attenuated radiation receivers may be employed such as a conventional solid state scintillation detector 95 shown in schematic fashion in FIG. 14. Yarn 97 is radiated by radioactive source 96 and the attenuated radiation is received by detector 95 which is in communication with a means to process data therefrom as elsewhere explained herein. A 500 volt power supply 27 furnishes d.c. current to ionization chamber 26 as is also seen in FIGS. 5 and 6. Hence, as one or more yarn strands 20' pass through entry nuclear detection sensor 12, a signal from ionization chamber 26 is directed along electrical line 28 (FIG. 1) to circuit board 18 where the signal is amplified and linearized and is then passed by electrical line 29 to computer 14. After passing by entry nuclear detection sensor 12, yarn strands 20' pass into slasher 11 where they encounter size box 15 which is filled with a liquid size 30 such as a natural or synthetic starch solution or the like. Strands 20 "pick-up" or are coated with size 30 where they then pass through squeeze rollers 16, 16'. Roller control 17 determines the pressure and thus the amount of size left on strands 20 as they pass therethrough. Conventional extractor 31 removes any excess size 30 from strands 20 whereas dryer 32 thereafter dries the sizing 30 applied. As would be understood, many different extractors, dryers and size applicators are in commercial use and can be incorporated into the invention herein. As yarn strands 20 leave slasher 11, exit nuclear detection sensor 13 is encountered and a like number of strands 20' are passed therein for exit radiation. Nuclear detection sensor 13 is substantially identical to entry nuclear detection sensor 12 as hereinbefore stated and sensor 13 relays signals through line 33 to circuit board 18' which amplifies and linearizes the signals therefrom before passing the modified signal through line 34 to computer 14. Once yarn strands 20 pass exit nuclear detection sensor 13 they are wound on loom beam 47 for transportation to a weaving mill or for subsequent operations.

As signals are received from entry and exit nuclear detection sensors 12 and 13, computer 14 which includes microprocessing circuitry is programmed to compare the signals received with known or theoretical standards, to thereby direct a signal through line 48 to squeeze roller control 17. The saving of data by computer 14 may be for example in fifty to one hundred yard increments for vehicle tire web processes and one to fifty yard increments for yarn sizing processes whereupon the very same increment is measured for each process and compared by computer 14 for the most accurate results and most precise size adjustment. Computer 14 includes a memory sufficient to internally or otherwise store the comparison values at all times during yarn processing. Thus, as required, rollers 16, 16' can tighten and thus reduce the amount of size 30 left on yarn 20, in size box 15 or rollers 16, 16' can loosen and allow a greater amount of size 30 to remain on yarn strands 20 passing therethrough. By carefully controlling the starch or other sizing agent applied, weaving efficiency can be greatly enhanced and the costs for the sizing materials reduced accordingly.

In order to calculate during yarn processing (size application), the percent of weight change in warp 40 (FIG. 2 consisting of yarn strands 20, 20') as shown in schematic representation, the amount of size 30 added to yarn strands 20 (percent size add-on) can be calculated as follows:

$$\% AO = \frac{W_2 - W_1}{W_1} \times 100$$

$\% AO = \%$ size add-on

Where:
$W_2$ = warp weight after processing
$W_1$ = warp weight before processing
With:

$$W_2 = D_2 \div [1 + (\% M_2/100)] \cdot \frac{Yd_1}{Yd_2}$$

Where:
$D_2$ = density of warp after processing
$\%S = \%$ stretch from entry measurement to exit measurement
$\%M_2 = \%$ moisture regain of warp after processing $$W_1 = \frac{D_1}{1 + (\% M_1/100)} \cdot \frac{1}{1 + (\% S/100)}$$

$Yd_1$ = yarn diameter in
$Yd_2$ = yarn diameter out
And:
$D_1$ = density of warp before processing
$\%M_1 = \%$ moisture regain of warp before processing
In order to measure the densities ($D_1$ and $D_2$), nuclear detection sensors 12 and 13 are utilized to provide a noncontact measurement of attenuated nuclear radiation (beta transmission) through yarn strands 20'. The accuracy achieved is plus or minus one-tenth of a gram per square meter ($0.1$ g/m$^2$) utilizing Technetium 99 as the radioactive iostope at a measurement range of 0 to 200 grams per square meter. Also utilized in the calculations is conventional electrical resistance moisture meter 23 to determine the moisture factor. Yarn elongation during processing is accounted for by pulse speed encoder 39 as seen in FIG. 8. Encoder 39 as seen in FIG. 1 is also in electrical communication with computer 14. Thus, computer 14 is programmed to account for the data received from encoders 39, 39', nuclear detection sensors 12 and 13 and moisture meters 23, 23' to thereby control or adjust squeeze rollers 16, 16' to insure the correct amount of size add-on is applied. Yarn evenness sensor 72 as seen in FIG. 10 may also be used in pairs, before and after size application during processing of unusually rough or uneven yarns or to account for increase in yarn diameter due to encapsulating size. Said evenness sensors would also be connected to computer 14 and accounted therefor in the programming of computer 14.

Another embodiment of the invention is shown in FIG. 3 whereby yarn web 50 is coated with sizing 66 or other suitable composition. As shown schematically in FIG. 4, web 50 comprises a series of warp yarns 51 which include a filling yarn 52 which is woven laterally thereacross which is longitudinally spaced approximately every two (2) to three (3) inches. As would be understood, since warp 50 is substantially unitary due to filling yarn 52, individual yarns 51 cannot be passed through pulleys 21 as seen in FIGS. 1, 5, 6 and 7. Warp 50 which may contain hundreds of yarns 51 has variations in density therealong which greatly affect the calculations and subsequent size pick-up required for uniformity. Adjustments must therefore be made for tire cord web 50 to insure the most efficient coating operation. Accordingly, conventional line scan digital cameras 62, 62' are utilized immediately after each nuclear detection sensors 55, 56. As shown in FIGS. 3, web 50 is delivered from creel 53 and passes over encoder roller 54 joined to encoder 57. Encoder 57 is in electrical communication with computer 65 as shown by broken line 58. An identical encoder 57' is connected to encoder roller 54' shown proximate loom beam 59. Web 50 passes through to entry nuclear detector sensor 55 which is structured similarly to sensor 12 as shown in FIG. 5 with the exception of pulleys 21 which are not provided for receiving yarn strands. Rather, radioactive source 60 which may contain Krypton 85 or other suitable isotopes is positioned below web 50 to radiate web 50 as it passes thereby. Moisture meter 61 is positioned aft entry nuclear detection sensor 55 and likewise is in communication with computer 65 as shown by dotted or broken line configuration. In order to provide an accurate measure of the density obtained by the use of nuclear detection sensor 55, since warp yarns 51 cannot be separated from web 50 or be individually accounted for, and due to the slight lateral movement of web 50 during processing, digital line scan cameras 62, 62' are employed. Line scan cameras 62, 62' are conventional industrial cameras adapted for use herewith and provides a uniform, approximately two inch diameter field or view area on web 50. Camera 62 as shown enlarged in FIG. 10 provides or compensates for variation in the tension of the web as it changes, i.e., the number of yarn strands under sensor 55. Light source 63, 63' is positioned beneath web 50, below respective cameras 62, 62'. As camera 62 provides a measurement of opacity, line scan digital camera 62 may have, for example 2048 pixels in linear array. Thus, variations in the number of warp yarns 51 under sensor 55 and the resultant density are compensated by digital camera 62 which is focused on the same area size to provide a uniform viewing width during yarn processing. Thus, the percent of coating pick-up from coating bath 66 is calculated as follows:

$$\% CPU = \frac{(W_2/\% O_2) - (W_1/\% O_1)}{(W_1/\% O_1)} \times 100$$

Where:
$W_2$ = tire cord web weight after processing = $D_2 \div [1+(\%M_2/100)]$
$W_1$ = tire cord web weight before processing
And:

$$\% O_2 = \begin{array}{c}\% \text{ opacity of tire} \\ \text{cord web after} \\ \text{processing}\end{array} = \frac{\text{\# of darkened pixels}}{2048} \times 100$$

$\%O_1$ = % opacity of tire cord web before processing

Thus, with the density measured by entry nuclear detection sensors 55 and 56, computer 65 is programmed to solve the calculation for percent CPU and to adjust and regulate controls 67 for rollers 68, 68' of coating bath 66 as illustrated in FIG. 3. Extractor 69 and oven 70 are conventional and are only shown in schematic fashion in FIG. 3. As hereinbefore explained, the entry and exit measurements of moisture meter 61, 61', nuclear detection sensors 55 and 56, digital cameras 62, 62' and encoders 57, 57' are accounted for by computer 65 which is programmed to assimilate the data and compare it to known values and to adjust vacuum pressure applied to extractor 69 to provide the proper and uniform coating on web 50.

While the embodiments herein have been presented separately, combinations of the components can be utilized to advantage under particular circumstances. For example, Krypton 85 as the radioisotope can be used in yarn processing and a digital camera positioned at the slasher after size add-on to provide an immediate squeeze rollers adjustment during yarn acceleration or deceleration as sometimes occurs in processing. Therefore, the illustrations and examples provided herein are for explanatory purposes and are not intended to limit the scope of the appended claims.

I claim:

1. A yarn sensor comprising: a yarn guide, means for generating radioactive emissions, said emissions generating means positioned proximate said yarn guide to radiate yarn passing along said yarn guide, means to detect radiation from said emissions generating means, said radiation detection means opposingly positioned from said emissions generating means relative to said passing yarn, a means to measure yarn opacity, said opacity measuring means positioned proximate said radiation detection means, a microprocessor, a yarn evenness sensor, said evenness sensor joined to said microprocessor and said microprocessor connected to said radiation detection means.

2. A yarn sensor as claimed in claim 1 wherein said yarn guide comprises a rotatable wheel.

3. A yarn sensor as claimed in claim 2 wherein said wheel comprises a pulley.

4. A yarn sensor as claimed in claim 3 wherein said pulley comprises a v-shaped groove.

5. A yarn sensor as claimed in claim 1 wherein said yarn guide comprises a pair of rotatable wheels, each of said wheels positioned on opposite sides of said generating means.

6. A yarn sensor as claimed in claim 1 wherein said radioactive generating means comprises a radioactive isotope.

7. A yarn sensor as claimed in claim 6 wherein said isotope comprises Technetium 99.

8. A yarn sensor as claimed in claim 6 wherein said isotope comprises Promethium 147.

9. A yarn sensor as claimed in claim 6 wherein said isotope comprises Krypton 85.

10. A yarn sensor as claimed in claim 6 wherein said isotope has an energy distribution of not greater than 0.3 MeV.

11. A yarn sensor as claimed in claim 1 wherein said detection means comprises an ion chamber.

12. A yarn sensor as claimed in claim 1 wherein said detection means comprises a solid state scintillation detector.

13. A yarn sensor as claimed in claim 1 and including a moisture sensor, said sensor joined to said yarn guide.

14. A yarn sensor as claimed in claim 1 and including a shutter, said shutter attached to said radioactive generating means to terminate radiation therefrom.

15. A yarn sensor apparatus for measuring the change in the density of processed yarn after sizing to control the sizing application comprising: a first nuclear emission sensor, a means to process electronic data, said first nuclear sensor in communication with said electronic data processing means, a second nuclear emission sensor, said second nuclear emission sensor in communication with said electronic data processing means, a sizing applicator, said sizing applicator positioned between said first emission sensor and said second emission sensor, said electronic data processing means communicating with said applicator, means to measure opacity, said opacity measuring means positioned proximate said first emission sensor, whereby said electronic data processing means controls the size applicator to regulate the amount of size applied to the yarn.

16. A yarn sensor apparatus as claimed in claim 15 wherein said nuclear emission sensor comprises: a yarn guide, means for generating radioactive emissions, said generating means positioned proximate said yarn guide to radiate yarn passing therethrough, means to detect radiation from said generating means, said detection means opposingly positioned from said generating means relative to said yarn.

17. A yarn sensor apparatus as claimed in claim 16 wherein said yarn guide comprises a rotatable wheel.

18. A yarn sensor apparatus as claimed in claim 15 wherein said radioactive generating means comprises a radioactive isotope.

19. A yarn sensor apparatus as claimed in claim 18 wherein said isotope has an energy distribution of not greater than 0.3 MeV.

20. A yarn sensor apparatus as claimed in claim 15 and including an encoder, said encoder positioned in contact with said yarn to measure the stretch thereof, said encoder in communication with said data processing means.

21. A yarn sensor apparatus as claimed in claim 15 wherein said opacity measuring means comprises a digital line scan camera, said camera positioned behind said first nuclear density sensor, said camera communicating with said data processing means for determining the opacity of said processed yarn.

22. A yarn sensor apparatus as claimed in claim 21 including a second digital line scan camera, said second digital camera positioned behind said second nuclear density sensor, said second digital camera communicating with said data processing.

23. A method for controlling the coating of yarn during processing by comparison to a known yarn density comprising the steps of:
(a) determining the density of the yarn before coating;
(b) sensing the evenness of the yarn;
(c) measuring the opacity of said yarn for use in density determination of the yarn;
(d) applying a coating to the yarn in a continuous process;
(e) determining the density of the yarn after coating;
(f) computing the differences between the determined densities;
(g) comparing the difference in density to a known density; and
(h) adjusting the coating application accordingly.

24. The method of claim 23 wherein the step of determining the density of the yarn before coating comprises: sensing a yarn increment with a nuclear density sensor, and transmitting data from the nuclear sensor to a means to process data.

25. The method of claim 23 wherein the step of applying coating to the yarn comprises: applying a sizing solution to a web of yarn and thereafter drying the web.

26. The method of claim 23 wherein the step of determining the density of the yarn after coating comprises: sensing the same increment of coated yarn as sensed before coating with a nuclear density sensor, and transmitting data from the nuclear density sensor to a means to process data.

27. The method of claim 23 wherein the step of computing the differences between the determined densities comprises: subtracting the density obtained before coating from the density obtained after coating.

28. The method of claim 23 wherein the step of comparing the differences in density to a known yarn density comprises: comparing the density difference to a theoretical yarn density.

29. The method of claim 23 wherein the step of adjusting the coating application comprises: decreasing the amount of coating applied to the yarn.

* * * * *